United States Patent [19]
Greco

[11] 3,953,509
[45] Apr. 27, 1976

[54] HYDROGENATION OF NITROBENZENE TO p-AMINOPHENOL

[75] Inventor: Nicholas P. Greco, Pittsburgh, Pa.

[73] Assignee: Koppers Company, Inc., Pittsburgh, Pa.

[22] Filed: Mar. 4, 1974

[21] Appl. No.: 447,848

Related U.S. Application Data

[63] Continuation of Ser. No. 296,260, Oct. 10, 1972, abandoned.

[52] U.S. Cl. ............................... 260/580; 260/575
[51] Int. Cl.² ........................................ C07C 85/10
[58] Field of Search ............................. 260/580, 575

[56] References Cited
UNITED STATES PATENTS

| | | |
|---|---|---|
| 2,198,249 | 4/1940 | Henke et al. ................... 260/575 |
| 2,765,342 | 10/1956 | Spiegler ........................... 260/575 |
| 3,328,465 | 6/1967 | Spiegler ........................... 260/580 |
| 3,336,386 | 8/1967 | Dovell et al. ................. 260/580 X |
| 3,350,450 | 10/1967 | Dovell et al. ..................... 260/575 |
| 3,761,425 | 9/1973 | Baessler et al. .............. 260/580 X |
| 3,803,054 | 4/1974 | Habig et al. .................. 260/580 X |

*Primary Examiner*—Helen M. S. Sneed
*Attorney, Agent, or Firm*—Robert D. Yeager; Robert DeMajistre

[57] ABSTRACT

A catalyst for use in preparing p-aminophenol by catalytic hydrogenation of nitrobenzene in an acidic solution. The catalyst is either powdered molybdenum sulfide-on-carbon or powdered platinum sulfide-on-carbon.

6 Claims, No Drawings

HYDROGENATION OF NITROBENZENE TO P-AMINOPHENOL

This is a continuation of application Ser. No. 296,260, filed Oct. 10, 1972, now abandoned.

FIELD OF THE INVENTION

The present invention relates to catalysts for use in the preparation of p-aminophenol from nitrobenzene and in particular to powdered molybdenum sulfide-on-carbon and powdered platinum sulfide-on-carbon.

BACKGROUND OF THE INVENTION

The catalytic hydrogenation of nitrobenzene in acidic solutions is generally well known. The process is believed to involve the formation of an intermediate product $\beta$-phenylhydroxylamine which is rearranged to form p-aminophenol and aniline. Illustrative of the processes for preparing p-aminophenol are U.S. Pat. Nos. 2,198,249, 2,765,342, 3,079,435, 3,265,735 and 3,383,416.

While sulfides of certain heavy metals such as cobalt, molybdenum, and tungsten have been proposed as hydrogenation catalysts, platinum and platinum on carbon and/or alumina are conventionally used in the conversion of nitrobenzene to p-aminophenol. While the conventional platinum catalysts are well suited for the preparation of commercially significant quantities of p-aminophenol, they are capable of further hydrogenating the p-aminophenol to alicyclic compounds which are undesirable by-products. This is particularly the case where hydrogenation takes place in the presence of a quantity of platinum catalysts.

Further, the nitrobenzene cannot be hydrogenated to completion without overhydrogenation by use of platinum catalysts. Thus, in the conventional hydrogenation reaction, the process must be stopped prior to completion to avoid the formation of undesired alicyclic compounds. This requires the additional step of recovering the unconsumed nitrobenzene by steam distillation.

Moreover, conventional platinum catalysts are easily poisoned and are not reusable unless returned to a precious metal refiner to recover the metal.

SUMMARY OF THE INVENTION

The present invention provides catalysts which are less expensive than conventional noble metal catalysts for use in the preparation of p-aminophenol. The catalysts of the present invention provide a complete hydrogenation of nitrobenzene without the possibility of overhydrogenation and with the consequential elimination of the usual nitrobenzene recovery step. Furthermore, the catalysts of the present invention are not readily poisoned during the preparation of p-aminophenol and can be reused many times before there is a loss of activity.

The catalysts of the present invention comprise powdered platinum sulfide-on-carbon and, preferably, powdered molybdenum sulfide-on-carbon. The powdered molybdenum sulfide-on-carbon catalyst of the present invention is much more active than molybdenum sulfide catalysts which have been previously prepared, particularly unsupported catalysts.

By using the molybdenum sulfide-on-carbon of the present invention, higher temperatures can be employed during hydrogenation. It is preferable to have the ability to operate at higher temperatures, e.g. 155°C, since the rearrangement of the intermediate $\beta$-hydroxylamine to p-aminophenol is not only endothermic but is significantly accelerated at the higher temperatures. Acceleration of the rearrangement is important, for if it does not take place, aniline is produced.

The catalysts of the present invention are powdered and of a size preferably equal to 200 mesh or better. The molybdenum sulfide catalyst is formed, for example, by dissolving molybdic oxide in water to which is added a powdered activated carbon. Hydrogen sulfide is added to saturate the solution to cause $MoS_3$-on-carbon to precipitate. While the catalyst can be reduced in a stream of hydrogen to activate it, it is preferably reduced in situ where the hydrogenation acid media comprises sulfuric acid. It has been found that in situ reduction provides a more active catalyst than those which have been pre-reduced.

The advantages of the present invention as well as the methods for employing the catalysts of the invention are more fully set forth in the following nonlimiting examples which comprise presently preferred embodiments of the invention.

PREFERRED EMBODIMENTS

Preparation of Powdered Molybdenum Sulfide-on-Carbon Catalyst

EXAMPLE 1

A mixture of water (430 g.) and molybdic oxide (50 g., 87 percent pure) was agitated at room temperature until the oxide nearly dissolved; ammonium hydroxide was then added until a clear solution was obtained. 50 g. of Darco G-60 (Atlas Powder activated carbon) was added to this solution with rapid agitation. The mixture was then saturated with $H_2S$. Conc. HCl was added to cause complete precipitation of $MoS_3$. The mixture was filtered and the colorless filtrate was discarded. Finally, the $MoS_3/c$ was washed with water until free of chlorides. After drying on a steambath, the catalyst (107 g.) was reduced in a stream of hydrogen at 400°C for 5 hours. The catalyst so obtained was pyrophoric.

EXAMPLE 2

41.5 percent molybdic acid (87 percent molybdic anhydride) was added to 600 ml. of water with agitation and 65 ml. of concentrated $NH_4OH$ to give a clear solution. $H_2S$ was added until saturated at which time deep reddish orange solids formed. 72 g. of Darco G-60 (Atlas Powder activated carbon) was added to the reaction mixture with agitation. 150 ml. of 30% conc. $H_2SO_4$ was then added dropwise until the solution had a pH of 1.5 $H_2S$ gas was evolved. The mixture was then filtered to give a water-white filtrate. The catalyst was washed with 3 × 600 ml. of distilled water. The catalyst, after partial air drying, contained 50 percent water and 25 percent molybdenum. The powdered $MoS_3$-on-carbon catalyst was activated "in situ" during hydrogenation of nitrobenzene.

Hydrogenation of Nitrobenzene in the Presence of Powdered Molybdenum Sulfide-on-Carbon Catalyst

EXAMPLE 3

A 1-gallon autoclave equipped with a glass liner, a Teflon-covered agitator, and a thermowell encased in Teflon, was charged with 450 g. of water (25 moles), 275 g. of sulfuric acid (2.7 moles), 160 g. of nitrobenzene (1.3 moles) and 5.0 g. of a once recycled 50 percent molybdenum sulfide-on-carbon catalyst. The reactor was heated to 155°C and maintained under 300 psi of $H_2$ for 11 hours after which absorption ceased. The product was found to be free of nitrobenzene. At the completion of the experiment, the vent gases were found to contain traces of $H_2S$. The hydrogenate was filtered while hot to recover 4.8 g. of catalyst. The filtrate was made ammoniacal to pH 9, cooled to 10°–15°C, and the precipitated violet colored crystals of p-aminophenol were filtered off. The crystals were rinsed with cold water to dissolve any salt present and finally with benzene to dissolve aniline present, then dried to give 93 g. (65.6 percent yield) of p-aminophenol. The aqueous filtrate was extracted with ethyl acetate. The extract was combined with the benzene washes and concentrated by distillation through a 30 inch packed column; the residual aniline was flash-distilled from p-aminophenol. Aniline (26 g., 22 percent yield, b.p. 60°C/6mm) was obtained overhead and 19 g. of crude p-aminophenol (13 percent yield) as the residue for a total yield of 78 percent.

EXAMPLES 4–14

Examples 4–14 were prepared similar to Example 3. However, various mineral acids including sulfuric, phosphoric, ammonium bisulfate and a mixture of sulfuric and ammonium bisulfate were used with 40 percent powdered molybdenum sulfide-on-carbon. The reaction temperature was 155°C with 300 psi $H_2$. The results of these experiments are set forth in Table I.

In Example 7, ammonium bisulfate was used and almost an equal yield of p-aminophenol and aniline were produced. Since ammonium bisulfate may be a desirable mineral acid, a combination of ammonium bisulfate and sulfuric acid was tried. The results of Examples 8, 9 and 10 show that the catalyst of the present invention provides high yields of p-aminophenol.

In Example 9, the powdered catalyst of the present invention was reduced in situ. The increased activity of the in situ reduced catalyst is demonstrated by the reduced reaction time, 8.5 hours compared with 11 to 14 hours with pre-reduced catalysts. It should be noted that reduction in situ is successful only when sulfuric acid is present in the reaction medium.

In Example 12, an emulsifying agent, Aliquat 26 (Rohm & Haas) was added to the reaction. The emulsifying agent, however, appeared to poison the reaction and no reduction was achieved.

In Examples 13 and 14, the reactants were saturated with $H_2S$ prior to reduction. The yield of p-aminophenol appeared to be less than those carried out under normal conditions. No reduction was achieved where ammonium bisulfate alone was used.

EXAMPLES 15–18

Hydrogenation of nitrobenzene was carried out as in Example 3. A 1-gallon autoclave agitated at 250 rpm was used at a temperature of 155°C and a hydrogen pressure of 250 psi. 4 g. of 25 percent $MoS_3$-on-carbon

TABLE I

Hydrogenation of Nitrobenzene/Rearrangement to p-Aminophenol
(Reduction Temp. 155°C.; Catalyst = 40% Molybdenum sulfide-on-carbon; 300 psi $H_2$)

| Examples | Acid Used | Acid Moles | Acid Conc.% | Consumed Nitrobenzene (Moles) | Molar Ratio Acid to $C_6H_5NO_2$ | Catalyst (g.) | Reaction Time, Hrs. | Product, Mole % Yield p-aminophenol | Aniline |
|---|---|---|---|---|---|---|---|---|---|
| 4 | $H_2SO_4$ | 2.75 | 30 | 1.33 | 2.1 | recycle[1] (5) | 12 | 78 | 17 |
| 5 | $H_2SO_4$ | 2.75 | 38 | 1.43 | 1.9 | recycle[2] (5) | 16 | 80 | 8 |
| 6 | $H_2SO_4$ | 2.75 | 38 | 0.95 | 2.9 | fresh[3] (4) | 12 | 78 | 10 |
| 7 | $NH_4HSO_4$ | 2.75 | 38 | 1.25 | 2.2 | recycle[1] (4) | 14 | 47 | 42 |
| 8 | 50%$H_2SO_4$ 50%$NH_4HSO_4$ | 2.66 | 38 | 1.13 | 2.4 | recycle[1] (4) | 14 | 72 | 22 |
| 9 | 50%$H_2SO_4$ 50%$NH_4HSO_4$ | 2.66 | 38.5 | 1.33 | 2.0 | fresh[4] (4) | 8.5 | 70 | 18 |
| 10 | 50%$H_2SO_4$ 50%$NH_4HSO_4$ | 2.66 | 38.5 | 1.33 | 2.0 | recycle[5] (3.9) | 9.5 | 70 | 18 |
| 11 | $H_3PO_4$ | 2.66 | 38 | 1.03 | 2.6 | recycle[1] (5) | 12 | 43 | 46 |
| 12 | 50%$H_2SO_4$ 50%$NH_4HSO_4$ | 2.66 | 38 | 1.33 | 2.0 | recycle[1] (5) | no reduction[6] | — | — |
| 13[7] | $NH_4HSO_4$ | 2.66 | 38 | 1.33 | 2.0 | fresh[4] (4) | no reduction | — | — |
| 14[7] | $H_2SO_4$ | 2.60 | 38 | 2.50 | 1.0 | fresh[4] (4) | 12 | 69.3 | 21.1 |

[1]Recycled pre-reduced.
[2]Recycled pre-reduced catalyst; after the 5th recycle of the catalyst.
[3]Pre-reduced at 400°C for 5 hrs.
[4]Not pre-reduced but reduced in situ.
[5]Catalyst was recycled from Example 9.
[6]0.8 g. Rohm & Haas Aliquat-26 added.
[7]Reduction mixture heavily sulfided with $H_2S$ before hydrogenation.

As can be seen from experiment 5, high yields of p-aminophenol were obtained utilizing a pre-reduced catalyst which had been used four times before.

was used as the catalyst. Varying ratios of sulfuric acid to nitrobenzene were tested. It was found that with a 25 percent $MoS_3$-on-carbon catalyst, a ratio of 2.1 -1.5 to 1 produced the best yields of p-aminophenol. The results of these tests are set forth in Table II.

TABLE II

| Examples | m.nitrobenzene Charged | m.nitrobenzene Consumed | $H_2SO_4$/ nitrobenzene Mole Ratio | Reaction Time,Hrs. | P-aminophenol[1] Aniline % Yield | | Reaction Rate[2] m./hr./g. |
|---|---|---|---|---|---|---|---|
| 15 | 1.30 | 1.30 | 2.1/1.0 | 8 | 67 | 15 | >.040 |
| 16 | 1.83 | 1.83 | 1.5/1.0 | 8 | 76.6 | 18 | >.057 |

TABLE II-continued

| Examples | m.nitro-benzene Charged | m.nitro-benzene Consumed | $H_2SO_4$/nitro-benzene Mole Ratio | Reaction Time,Hrs. | P-amino-phenol[1] Aniline % Yield | | Reaction Rate[2] m./hr./g. |
|---|---|---|---|---|---|---|---|
| 17 | 2.20 | 2.14 | 1.25/1.0 | 8 | 61 | 19 | .067 |
| 18 | 2.70 | 2.37 | 1.0/1.0 | 10 | 59 | 19 | .060 |

[1]p-aminophenol yield calcd. from VPC analyses of crude product, based on nitrobenzene consumed.
[2]Expressed as moles of nitrobenzene consumed per hour per gram of catalyst.

Hydrogenation of Nitrobenzene in the Presence of Powdered Platinum Sulfide-on-Carbon Catalyst

EXAMPLE 19

300 g. nitrobenzene (2.44 moles), 300 g. 96 percent sulfuric acid (2.96 moles) and 2 g. of 5 percent PtS-on-carbon (Engelhard) containing 50 percent water, and 300 g. water (16.7 moles) were added to a glass lined autoclave and agitated with a Teflon-coated stirrer. The mixture was heated at 132°–135°C under 200–500 psi of hydrogen for 18 hours. The hydrogenate was steam-distilled to give 20.1 g. of nitrobenzene in the distillate. The hot aqueous charge was filtered to recover the catalyst. The filtrate was cooled to room temperature and $NH_4OH$ added until a pH 9 was achieved. The precipitate, p-aminophenol, was filtered off and washed with water and benzene on the filter. The filtrate was extracted with ethyl acetate and the extract distilled at atmospheric pressure. The residue, a mixture of aniline and p-aminophenol, was distilled on a steam bath under vacuum to give 16 g. (7.5 percent) aniline, b.p. 80°C/20mm. The solid (35 g.) remaining as a residue was combined with the solid on the filter and dried under vacuum to give a total of 193 g. (78 percent yield) of crude p-aminophenol. (Purity of the p-aminophenol was not determined).

EXAMPLES 20–31

Tests were run similar to that of Example 19 in which the conditions of hydrogenation were varied. The variable included time, temperature, pressure, molar ratios of acid to nitrobenzene, acid and acid concentration and catalyst concentration. The results of these tests are set forth in Table III.

TABLE III

Hydrogenation of Nitrobenzene and Rearrangement to P-aminophenol in Presence of Sulfided 5% Platinum Catalyst[3] and Various Acids

| Example | Nitro-Benzene (Moles Consumed) | Acid Used (Moles) | Acid conc. (%) | Catalyst (g.) | Hydrogen Pressure (psig) | Temp. °C. | Time hrs. | Product, Mole % Yield p-aminophenol[1,4] | Aniline[2] | Unaccounted For (%) |
|---|---|---|---|---|---|---|---|---|---|---|
| 20 | 2.44 | $H_2SO_4$(2.6) | 40 | 1.0 | 450–500 | 135 | 5.5 | 59 | 4.0 | 37 |
| 21 | 2.20 | $H_2SO_4$(2.6) | 40 | 3.0 | 300 | 120 | 7 | 9 | 70 | 21 |
| 22 | 1.70 | $H_2SO_4$(2.6) | 40 | 3.0 | 300 | 135 | 4.5 | 60 | 5 | 35 |
| 23 | 2.2 | $H_2SO_4$(1.7) | 30 | 3.0 | 200–500 | 125 | 5 | 58 | 7 | 35 |
| 24 | 2.4 | $H_2SO_4$(2.8) | 38 | 3.0 | 200–500 | 135 | 8.5 | 82 | 18 | 0 |
| 25 | 1.7 | $H_2SO_4$(2.8) | 38 | 2.0 | 200–500 | 137 | 8.5 | 50 | 15 | 35 |
| 26 | 1.9 | $H_2SO_4$(2.8) | 38 | 2.0 | 200–500 | 148 | 8 | 69 | 15 | 16 |
| 27 | 1.4 | $H_2SO_4$(2.8) | 38 | 3.0 | 150 | 120 | 4.5 | 30 | 36 | 34 |
| 28 | 1.1 | $NH_4HSO_4$(2.8) | 38 | 3.0 | 150 | 130 | 5 | 61 | 29 | 10 |
| 29 | 1.3 | $NH_4HSO_4$(2.5) | 40 | 3.0 | 200 | 135 | 4.5 | 61 | 31 | 8 |
| 30 | 2.4 | $NH_4HSO_4$(2.6) | 50 | 3.0 | 400–500 | 135 | 12 | 52 | 5) | 5) |
| 31 | 2.4 | $H_3PO_4$(2.6) | 37 | 3.0 | 200–300 | 135 | 5 | 61 | 19 | 20 |

[1]Crude yield, based on nitrobenzene consumed.
[2]Implied yield; by distillation.
[3]50% wet with water.
[4]Purity not determined.

While presently preferred embodiments of the invention have been described in particularity, it may otherwise be embodied within the scope of the appended claims.

What is claimed is:

1. In a method for the preparation of p-aminophenol by reducing nitrobenzene with hydrogen at elevated temperatures in an acid solution and in the presence of a catalyst, the improvement comprising a catalyst selected from the group consisting of powdered molybdenum sulfide-on-carbon and powdered platinum sulfide-on-carbon.

2. The improvement set forth in claim 1 wherein the said temperature is from 135° to 155°C.

3. The improvement set forth in claim 2 wherein the ratio of acid present to nitrobenzene is 1.5 – 2.9 to 1.

4. The improvement set forth in claim 3 wherein said catalyst is present in an amount from 1 to 5 percent.

5. The improvement set forth in claim 1 wherein said catalyst is molybdenum sulfide-on-carbon.

6. The improvement set forth in claim 5 wherein the acidic solution includes sulfuric acid and said catalyst is reduced in situ.

* * * * *